(12) United States Patent
Giuliani et al.

(10) Patent No.: US 8,729,033 B2
(45) Date of Patent: May 20, 2014

(54) THERAPEUTIC, DIETARY OR COSMETIC USE OF COMPOUNDS WITH SPECIFIC ANTI-APOPTOTIC ACTIVITY TOWARD CASPASE-3, AND COMPOSITIONS CONTAINING THESE COMPOUNDS

(75) Inventors: Giammaria Giuliani, Milan (IT); Anna Benedusi, Milan (IT); Sergio Baroni, Villa d'Adda (IT)

(73) Assignee: Giuliani S.p.A., Milan (IT)

( * ) Notice: Subject to any disclaimer, the term of this patent is extended or adjusted under 35 U.S.C. 154(b) by 13 days.

(21) Appl. No.: 13/127,446

(22) PCT Filed: Oct. 30, 2009

(86) PCT No.: PCT/EP2009/064368
§ 371 (c)(1),
(2), (4) Date: May 3, 2011

(87) PCT Pub. No.: WO2010/060729
PCT Pub. Date: Jun. 3, 2010

(65) Prior Publication Data
US 2011/0218164 A1     Sep. 8, 2011

(30) Foreign Application Priority Data
Nov. 3, 2008 (EP) ..................................... 08425704

(51) Int. Cl.
*A61K 31/047* (2006.01)
*C07H 17/07* (2006.01)

(52) U.S. Cl.
CPC ..................................... *C07H 17/07* (2013.01)
USPC .............................. 514/27; 514/674; 514/729

(58) Field of Classification Search
CPC ....................................................... C07H 17/07

USPC ............................................ 514/27, 674, 729
See application file for complete search history.

(56) References Cited

U.S. PATENT DOCUMENTS

| 6,254,898 B1 | 7/2001 | Bragaglia |
| 6,573,299 B1 * | 6/2003 | Petrus ........................... 514/558 |
| 2006/0264357 A1 * | 11/2006 | Zikria et al. ...................... 514/6 |

FOREIGN PATENT DOCUMENTS

| WO | WO 96/10387 | | 4/1996 | |
| WO | WO 02/05776 | | 1/2002 | |
| WO | WO 03/063851 | | 8/2003 | |
| WO | WO 2004/069186 | | 8/2004 | |
| WO | WO 2007/046083 | * | 4/2007 | ........... A61K 31/192 |
| WO | WO 2008/114141 | | 9/2008 | |

OTHER PUBLICATIONS

Sujak et al., "Lutein and zeaxanthin as protectors of lipid membranes against oxidative damage: The structural aspects", Arch. of Biochem. and Biophysics vol. 371, No. 2, pp. 301-307 (1999).

* cited by examiner

*Primary Examiner* — Brandon Fetterolf
*Assistant Examiner* — Yih-Horng Shiao
(74) *Attorney, Agent, or Firm* — DLA Piper LLP (US)

(57) ABSTRACT

This invention regards the use of zeaxanthin and/or rutin, as such or further combined with spermidine, as the active principle in a pharmaceutical, dietary, or cosmetic composition, acting to inhibit caspase-3 and therefore to control apoptosis by preventing programmed cell death.
The indication for this composition according to the invention is primarily the treatment of scalp disorders characterized by excessive cellular turnover including chemotherapy-induced alopecia, alopecia areata, androgenetic alopecia and telogen effluvium.

18 Claims, 2 Drawing Sheets

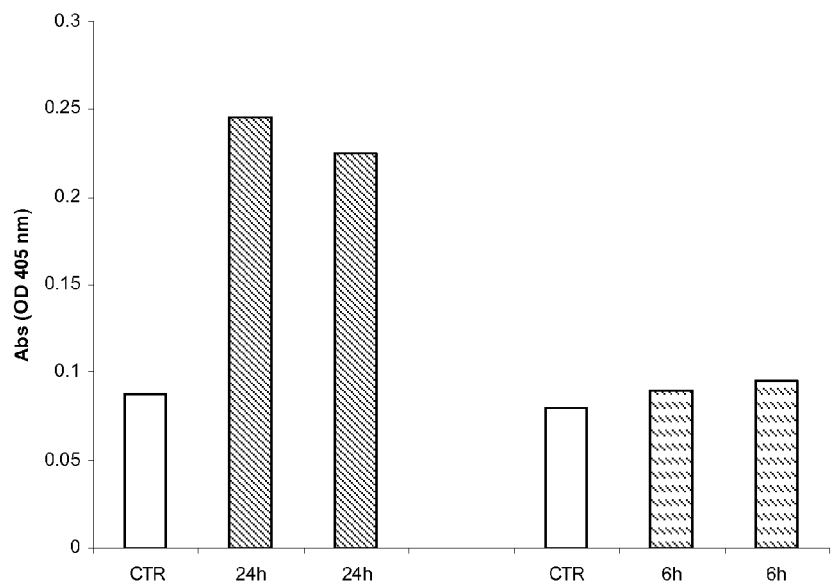
Fig. 1 - Induction of caspase-3 activity in the presence of Staurosporine (1µM).
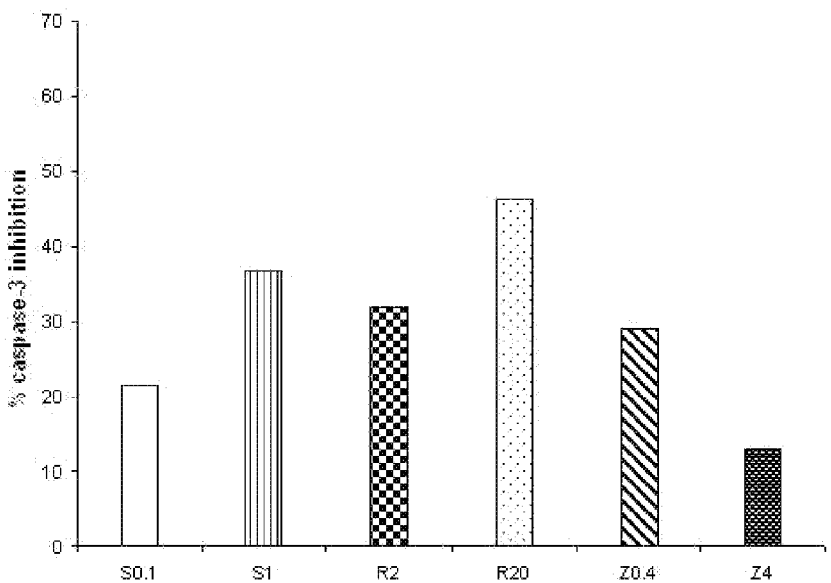
Fig. 2 – Anti-apoptotic effect of the active ingredients used individually

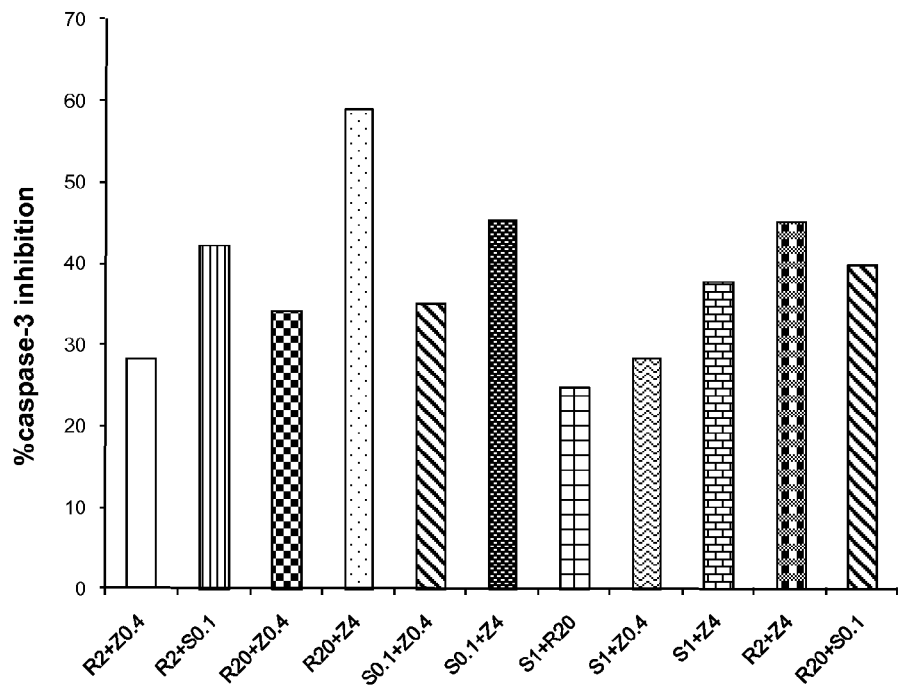
Fig. 3 – Anti-apoptotic effect of pairs of active ingredients
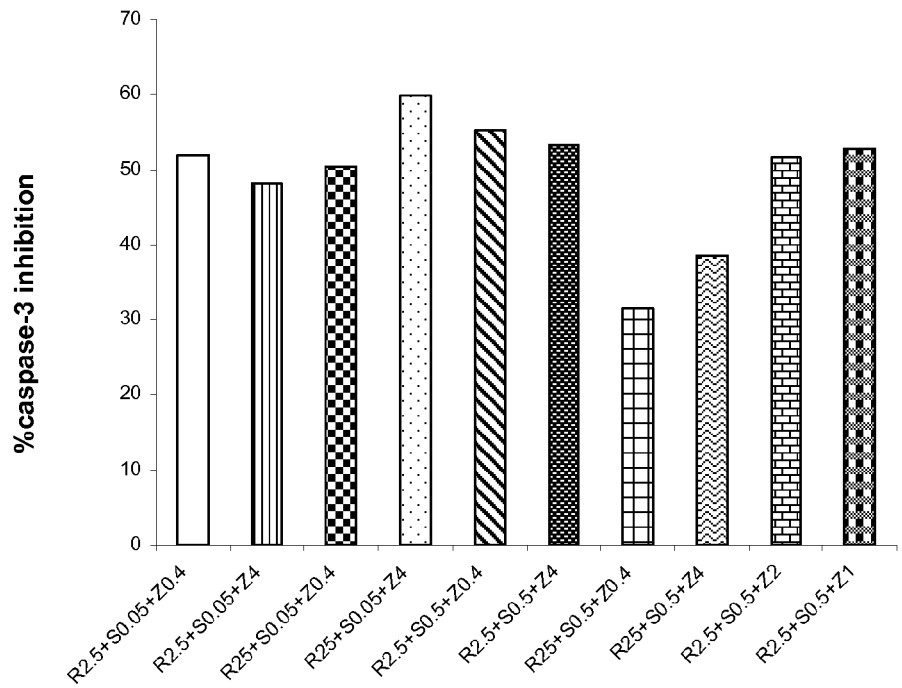
Fig. 4 – Anti-apoptotic effect of ternary combinations of active ingredients

THERAPEUTIC, DIETARY OR COSMETIC USE OF COMPOUNDS WITH SPECIFIC ANTI-APOPTOTIC ACTIVITY TOWARD CASPASE-3, AND COMPOSITIONS CONTAINING THESE COMPOUNDS

FIELD OF THE INVENTION

The invention regards the use of compounds that have been found to be active in the inhibition of caspase-3, and therefore useful for controlling apoptosis by preventing programmed cell death in the treatment of diseases and dysfunctions characterized by a defect in the regulation of the physical mechanisms of apoptosis and by consequently early cell death.

PRIOR ART

One of these dysfunctions is typically alopecia. The life cycle of the hair follice is essentially represented by three successive phases: anagen (growth), catagen (involution) and telogen (resting phase). At the end of the last phase, the cycle begins again. The biological basis of this phenomenon resides in the capacity of the follicle's stem cells to exit, at alternate phases, from their state of quiescence. During follicle growth and hair production, the activity of growth factors regulating proliferation, differentiation, and survival predominates. The regression phase, instead, is characterized by the activation of molecular pathways that induce apoptosis in the follicle cells.

Distinct cellular populations in the hair follicle possess differential susceptibility to apoptotic phenomena. In particular, epithelial cells and melanocytes are the most sensitive, while dermal fibroblasts, some keratinocytes, and some melanocytes selected for survival seem to be more resistant. The life cycle of the hair and its development depend on growth factors that regulate communication signals between the epithelium and mesenchymal cells of the follicle. These molecular factors belong to the following protein families: BMP (Bone Morphogenetic Protein), TGF-beta, EGF, FGF, IGF, neurotrophin, TNF, and Wnt.

Apoptosis, also called programmed cell death, is a complex biological process that is regulated at a gene level and that plays a crucial role in tissue homeostasis, where it counteracts the proliferative (mitotic) action exerted by growth factors. From a morphological point of view, a cell in apoptosis undergoes a rapid reduction of volume, accompanied by condensation and the loss of contact with surrounding cells. At a nuclear level, disaggregation, the break-up of the membrane, and the condensation and fragmentation of the chromatin into fragments of about 200 base pairs is observed.

The caspases, catalytic enzymes, are a protein component essential for both the activation and implementation of the apoptotic process. 10 caspases have been identified in the human (in fact, they are numbered from 1 to 10). The caspases are catalytic enzymes that exert protease activity and function both as effectors in the cellular disassembly typical of apoptosis and as initiators of this phenomenon following activation by pro-apoptotic signals.

Caspase-3 (also known as CPP32, Yama, or apopain) is one of the principal effectors of apoptosis.

Under conditions of quiescence, in most cells, caspase-3 exists in an inactive form (proenzyme) that, following pro-apoptotic stimuli, is activated by caspase-8 or by caspase-9. This depends on the type of apoptotic stimulus received by the cell.

Apoptosis is therefore considered to have a central role in regulating the regression of the hair follicle (Effects of finasteride on apoptosis and regulation of the human hair cycle, Keane et al., *Journal of Cutaneous Medicine and Surgery*, vol. 6, no. 1, January 2002).

SUMMARY OF THE INVENTION

Surprisingly, it is now found that some compounds, used both alone and in combination, may have an inhibitory effect on caspase-3, have a potent anti-apoptotic activity, and can counteract hair loss.

According to the invention, in fact, a primary application of these compounds equipped with specific caspase-3 inhibitory activity regards disorders of the scalp characterized by excessive cellular turnover, such as chemotherapy-induced alopecia, alopecia areata, androgenetic alopecia and telogen effluvium.

DETAILED DESCRIPTION OF THE INVENTION

In this regard, this invention addresses the use of zeaxanthin and/or rutin, as such or further combined with spermidine, as the active principle in a pharmaceutical, dietary, or cosmetic composition suitable to inhibit the activity of the caspase-3 enzyme and therefore to control apoptosis by preventing programmed cell death, for every indication in which this inhibitory effect is useful. Particular reference is made to the treatment of alopecia in humans through caspase inhibition.

The invention also regards a pharmaceutical, dietary, or cosmetic composition suitable to inhibit the activity of the caspase-3 enzyme and therefore to control apoptosis by preventing programmed cell death characterized by comprising zeaxanthin and/or rutin, as such or further combined with spermidine, as the active principle formulated with every appropriate excipient for topical or systemic (preferably orally) administration.

An experimental study reported in the remainder of this description has in fact surprisingly demonstrated that it is possible to obtain inhibition of the apoptotic activity of caspase-3 in a relevant way by using the compounds according to the present invention.

The indications for this pharmaceutical, dietary, or cosmetic composition according to the invention are therefore principally the treatment of scalp disorders characterized by excessive cellular turnover, including chemotherapy-induced alopecia, alopecia areata, androgenetic alopecia and telogen effluvium.

The invention refers to the use, as active ingredients, of the compounds zeaxanthin or rutin individually, or paired with one another, each one paired with spermidine, or both in combination with spermidine.

In one embodiment, the invention's composition includes zeaxanthin or rutin.

In a different embodiment, the invention's composition includes zeaxanthin and rutin. In a corresponding embodiment, the invention's composition includes 2 mg of zeaxanthin and 2.5 mg of rutin.

In a preferred embodiment, the invention's composition includes zeaxanthin, rutin, and spermidine. In a corresponding form of preferred implementation, the invention's composition includes zeaxanthin, rutin, and spermidine in a weight relationship of approximately 8:5:1, respectively. In a further form of preferred implementation, the invention's composition includes zeaxanthin, rutin, and spermidine in a weight relationship of approximately 4:5:1, respectively.

In a different embodiment, the invention's composition includes an active principle which consists of rutin and spermidine. In a corresponding embodiment, the invention's composition includes rutin and spermidine in a weight relationship of approximately 5:1.

In a different embodiment, the invention's composition includes zeaxanthin and spermidine. In a corresponding embodiment, the invention's composition includes zeaxanthin and spermidine in a weight relationship of approximately 4:1.

In a embodiment, the invention's composition includes excipients for topical administration to the scalp. Suitable concentrations are chosen from among: 0.0005-1% w/w zeaxanthin, 0.0005-1% w/w rutin, and 0.0001-1% w/w spermidine HCl.

In a different embodiment, the invention's composition includes excipients for systemic administration, preferably orally. In a preferred embodiment, a composition for oral use, including a tablet, includes 2 mg zeaxanthin, 2.50 mg rutin, and 0.50 mg spermidine trihydrochloride.

The following examples illustrate the invention without in any way limiting its scope.

EXAMPLE 1

Dietary supplement in tablets for oral use with Zeaxanthin, Rutin, Spermidine, sulfur donating compounds (sulfurated amino acids, methylsufonylmethane), vitamins and minerals.
Every tablet contains:

| | |
|---|---|
| Methionine | 300 mg |
| Spermidine trihydrochloride | 0.5 mg |
| Rutin | 2.5 mg |
| Zeaxanthin | 2 mg |
| Calcium pantothenate | 9 mg |
| d-Biotin | 0.05 mg |
| Zinc amino acid chelate | 37.5 mg (equivalent to 7.5 mg of Zinc) |
| Copper amino acid chelate | 12 mg (equivalent to 1.2 mg of Copper) |
| Vitamin C (ascorbic acid) | 90 mg |
| Vitamin B6 hydrochloride | 2.421 mg (equivalent to 2 mg of Pyridoxine). |
| Vitamin E acetate (dl-alpha tocopherol) | 15 mg |
| Folic acid | 0.3 mg |
| Microcrystalline cellulose | 60-150 mg |
| Calcium phosphate dibasic dihydrate | 60-150 mg |
| Hydroxypropyl methylcellulose | 50-100 mg |
| Gum arabic | 2-20 mg |
| Magnesium stearate | 5-9 mg |
| Silicon dioxide | 2.50-8 mg |
| Yellow iron oxide E172 | 0.1-0.3 mg |
| Copper chlorophyll | 0.4-0.8 mg |
| Titanium dioxide | 1.5-3.5 mg |
| Stearic acid | 1-2 mg |
| Ethylcellulose | 2-3 mg |
| Hydrolyzed gelatin | 15-17 mg |

EXAMPLE 2

Dietary supplement in hard capsules with Zeaxanthin, Rutin, and Spermidine.

Every capsule contains:

| | |
|---|---|
| Spermidine trihydrochloride | 0.5 mg |
| Rutin | 2.5 mg |
| Zeaxanthin | 2 mg |
| Microcrystalline cellulose | 100-150 mg |
| Calcium phosphate dibasic dihydrate | 100-150 mg |
| Magnesium stearate | 3-6 mg |
| Silicon dioxide | 2.5-5 mg |
| Natural gelatin (packaging) | q.s. |

EXAMPLE 3

Dietary supplement in tablets for oral use with Zeaxanthin, Rutin, Spermidine, soy isoflavones, dry extract of *Emblica officinalis*, resveratrol, vitamins, and minerals.
Every tablet contains:

| | |
|---|---|
| Soy isoflavones | 40 mg |
| Calcium pantothenate | 9 mg |
| d-Biotin | 0.5-0.15 mg |
| Spermidine trihydrochloride | 0.5 mg |
| Rutin | 2.5 mg-12 mg |
| Dry extract of *Emblica officinalis* | 100 mg |
| Resveratrol | 0.5 mg |
| Zeaxanthin | 2 mg |
| Zinc amino acid chelate | 37.5 mg (equivalent to 7.5 mg of zinc) |
| Copper amino acid chelate | 12 mg (equivalent to 1.2 mg of Copper) |
| Folic acid | 0.2-0.3 mg |
| Microcrystalline cellulose | 60-150 mg |
| Calcium phosphate dibasic dihydrate | 100-300 mg |
| Hydroxypropyl methylcellulose | 40-120 mg |
| Tapioca dextrin | 40-100 mg |
| Gum arabic | 2-20 mg |
| Glyceryl behenate | 5-10 mg |
| Silicon dioxide | 2.5-10 mg |
| Yellow iron oxide E172 | 0.1-0.3 mg |
| Red iron oxide E172 | 0.1-0.3 mg |
| Titanium dioxide | 1.5-3.5 mg |
| Stearic acid | 1-2 mg |

EXAMPLE 4

Extemporaneous non-effervescent granulated, with a base of sulfur donating compounds (methylsulfonylmethane) and Zeaxanthin.
Every dose contains:

| | |
|---|---|
| Methylsulfonylmethane | 200 mg |
| Zeaxanthin | 2 mg |
| Maltitol powder | 100-300 mg |
| Sodium starch glycolate | 100-300 mg |
| Gum arabic | 100-500 mg |
| Sorbitol powder | 5-9 mg |
| Acesulfame potassium | 0.5-1.5 mg |
| Aspartame | 0.25-1.25 mg |
| Sodium stearyl fumarate | 10-30 mg |
| Flavoring | q.s. |

EXAMPLE 5

Dietary supplement tablets for oral use with Zeaxanthin, Rutin, Spermidine, L-Arginine, *Ajuga reptans*, Quercetin, vitamins, and minerals.

Every tablet contains:

| | |
|---|---|
| Rutin | 2.5 mg |
| Zeaxanthin | 2 mg |
| Spermidine trihydrochloride | 0.5 mg |
| Calcium d-Pantothenate | 9 mg |
| d-Biotin | 0.15 mg |
| Quercitin | 0.9 mg |
| Borage oil (omega-6 polyunsaturated fatty acids) | 40-100 mg |
| Rutin | 3-12 mg |
| L-Arginine hydrochloride | 242 mg |
| Dry extract of *ajuga reptans* | 5 mg |
| Zinc amino acid chelate | 37.5 mg (equivalent to 7.5 mg of zinc) |
| Copper amino acid chelate | 12 mg (equivalent to 1.2 mg of Copper) |
| Tapioca dextrin | 40-100 mg |
| Microcrystalline cellulose | 130-200 mg |
| Calcium phosphate dibasic dihydrate | 50-200 mg |
| Hydroxypropyl methylcellulose | 40-100 mg |
| Mono- and diglycerides of fatty acids | 5-10 mg |
| Silicon dioxide | 5-10 mg |
| Stearic acid | 1-2 mg |
| Titanium dioxide | 1.5-3.5 mg |
| Red iron oxide | 0.1-0.3 mg |
| Riboflavin (coloring agent) | 0.1-0.3 mg |

EXAMPLE 6

Dietary supplement in tablets for oral use with lactic acids and nutrients useful for rebalancing scalp flaking.
Every tablet contains:

| | |
|---|---|
| Rutin | 2.5 mg |
| Zeaxanthin | 2 mg |
| *Lactobacillus rhamnosus* | $10^9$ cfu/tab (1 billion cfu/g) |
| Insoluble dietary fiber | 20-40 mg |
| Inulin | 20-40 mg |
| Methionine | 200 mg |
| Vitamin B5 (Calcium pantothenate) | 9 mg |
| Vitamin B6 hydrochloride | 2.421 mg (equivalent to 2 mg of Pyridoxine). |
| Biotin | 0.23 mg |
| Vitamin A | 1200 mcg |
| Vitamin B2 (Riboflavin) | 1.60 mg |
| Dry extract of *Ajuga reptans* leaves | 2.5 mg |
| Zinc amino acid chelate | 37.5 mg (equivalent to 7.5 mg of Zinc) |
| Vitamin C (ascorbic acid) | 90 mg |
| Vitamin E acetate (dl-alpha tocopherol) | 15 mg |
| Selenium yeast | 15 mg (equivalent to 30 mcg of Selenium) |
| Tricalcium phosphate | 28-32 mg |
| Microcrystalline cellulose | 100-200 mg |
| Anhydrous calcium hydrogen phosphate | 50-100 mg |
| Magnesium stearate | 6-10 mg |
| Silicon dioxide | 4-10 mg |

EXAMPLE 7

Styling gel with Zeaxanthin, Rutin, Spermidine.

| Name INCI Ingredients | % w/w |
|---|---|
| Polyacrylate-14 | 0.7-2 |
| Hydroxypropyl guar | 0.5-5 |
| Sodium Hydroxymethylglycinate | 0.1-1 |
| Benzophenone-4 | 0.1-3 |
| Tetrasodium EDTA | 0.1-0.8 |
| Taurine | 0.01-0.08 |
| Calcium pantothenate | 0.01-0.05 |
| *Ajuga reptans* extract with phenylpropanoid content >50% | 0.001-0.1 |
| Zeaxanthin | 0.001-0.1 |
| Rutin | 0.005-0.05 |
| Spermidine HCl | 0.001-0.05 |
| Biotin | 0.0001-0.05 |
| Water | q.s. to 100 |

EXAMPLE 8

Fortifying airless mousse with Zeaxanthin, Rutin, and Spermidine.

| Name INCI Ingredients | % w/w |
|---|---|
| ALCOHOL | 9.5-20 |
| *BOEHMERIA NIPONONIVEA* LEAF EXTRACT | 1-5.5 |
| TAURINE | 1-5.5 |
| GLYCERIN | 1-3.5 |
| SODIUM OLIVE AMPHOACETATE | 0.5-2 |
| CALCIUM PANTOTHENATE | 0.1-2 |
| TOCOPHEROLS ($\alpha,\beta,\gamma$) | 0.1-2 |
| POLYQUATERNIUM-16 | 0.02-1 |
| DISODIUM EDTA | 0.02-0.08 |
| *AJUGA REPTANS LEAF* EXTRACT | 0.02-0.05 |
| SPERMIDINE HCl | 0.01-0.05 |
| ZEAXANTHIN | 0.1-0.5 |
| RUTIN | 0.1-0.5 |
| POTASSIUM METABISULFITE | 0.01-0.05 |
| *VITIS VINIFERA* | 0.01-0.05 |
| BIOTIN | 0.002-0.05 |
| CITRIC ACID | 0.1-0.3 |
| Water | q.s. to 100 |

EXAMPLE 9

Fortifying hair lotion with Zeaxanthin, Rutin, and Spermidine.

| Name INCI Ingredients | % w/w |
|---|---|
| Alcohol | 10.5-20 |
| *Juglans regia* extract | 1-4.5 |
| PEG-40 Hydrogenated castor oil | 0.5-3 |
| Calcium pantothenate | 0.1-0.5 |
| Perfume | 0.1-0.5 |
| Disodium EDTA | 0.05-0.1 |
| Citric acid | 0.05-0.1 |
| *Ajuga reptans* leaf extract | 0.05-0.1 |
| Spermidine HCl | 0.01-0.05 |
| Zeaxanthin | 0.1-0.3 |
| Rutin | 0.1-0.5 |
| Biotin | 0.003-0.05 |
| Lecithin | 0.002-0.005 |
| Polysorbate 80 | 0.001-0.005 |
| Water | q.s. to 100 |

EXAMPLE 10

Restructuring conditioner with Zeaxanthin, Rutin, and Spermidine.

| Name INCI Ingredients | % w/w |
|---|---|
| CETEARYL ALCOHOL | 1.5-5.5 |
| DIMETHICONE | 3-4.5 |
| GLYCERYL STEARATE | 4-5.5 |
| C12-13 ALKYL LACTATE | 1.5-3 |
| CETRIMONIUM CHLORIDE | 1-3.5 |
| PEG-100 STEARATE | 1-3.5 |
| DIMETHICONOL | 1-2.5 |
| XYLITOL | 1-2.5 |
| PHENOXYETHANOL | 0.5-1 |
| PROPYLENE GLYCOL | 0.5-1 |
| HYDROXYETHYL CELLULOSE | 0.5-1 |
| PANTHENOL | 0.5-1 |
| PERFUME | 0.5-1 |
| TRIMETHYLSILYLAMODIMETHICONE | 0.2-1 |
| METHYLPARABEN | 0.1-1 |
| DISODIUM EDTA | 0.1-1 |
| BUTYLENE GLYCOL | 0.1-1 |
| ETHYLPARABEN | 0.01-0.05 |
| LACTIC ACID | 0.01-0.05 |
| PROPYLPARABEN | 0.01-0.05 |
| CALCIUM PANTOTHENATE | 0.001-0.005 |
| ZEAXANTHIN | 0.0005-0.01 |
| RUTIN | 0.0005-0.01 |
| SPERMIDINE HCl | 0.0001-0.005 |
| BIOTIN | 0.00001-0.0005 |
| WATER | q.s. to 100 |

EXAMPLE 11

Anti-hair loss mask gel with Zeaxanthin, Rutin, and Spermidine.

| Name INCI Ingredients | % w/w |
|---|---|
| GLYCERIN | 1.5-4.5 |
| "AMMONIUM ACRYLOYL-DIMETHYL TAURATE/VP COPOLYMER" | 1-5.5 |
| CYCLOPENTASILOXANE | 1-5.5 |
| PHENOXYETHANOL | 0.1-0.8 |
| PERFUME | 0.1-0.5 |
| SILICONE QUATERNIUM-15 | 0.1-0.5 |
| TOCOPHERYL ACETATE | 0.1-0.5 |
| DIMETHICONE | 0.1-0.3 |
| METHYLPARABEN | 0.1-0.5 |
| AMMONIUM GLYCYRRHIZATE | 0.1-0.5 |
| ETHYL HEXYL METHOXYCINNAMATE | 0.05-0.1 |
| DISODIUM EDTA | 0.05-0.1 |
| ETHYLPARABEN | 0.02-0.05 |
| GLYCERYL LAURATE | 0.02-0.05 |
| CALCIUM PANTOTHENATE | 0.02-0.05 |
| PROPYLPARABEN | 0.02-0.05 |
| ZEAXANTHIN | 0.001-0.1 |
| RUTIN | 0.01-0.1 |
| SPERMIDINE HCL | 0.001-0.005 |
| BIOTIN | 0.0001-0.005 |
| WATER | q.s. to 100 |

EXAMPLE 12

Fortifying shampoo with Zeaxanthin, Rutin, and Spermidine.

| Name INCI Ingredients | % w/w |
|---|---|
| MAGNESIUM LAURETH SULFATE | 2-8.5 |
| SODIUM LAUROYL SARCOSINATE | 2-5.5 |
| DISODIUM LAURETH SULFOSUCCINATE | 1-5.5 |
| PEG-200 HYDROGENATED GLYCERYL PALMATE | 1-5.5 |
| COCAMIDE MIPA | 1-5.5 |
| GLYCERIN | 0.5-1 |
| PERFUME | 0.5-1 |
| GLYCOL DISTEARATE | 0.5-1 |
| CITRIC ACID | 0.5-1 |
| LAURETH-7 | 0.5-1 |
| PEG-7 GLYCERYL COCOATE | 0.5-1 |
| BETAINE | 0.5-1 |
| LAURYL METHYL GLUCETH-10 HYDROXYPROPYLDIMONIUM CHLORIDE | 0.5-1 |
| POLYQUATERNIUM-10 | 0.2-0.5 |
| SODIUM HYDROXYMETHYLGLYCINATE | 0.2-0.5 |
| POTASSIUM UNDECYLENOYL WHEAT PROTEIN | 0.2-0.5 |
| TETRASODIUM EDTA | 0.2-0.5 |
| PANTHENOL | 0.2-0.5 |
| SILICONE QUATERNIUM-15 | 0.1-0.5 |
| SILK AMINO ACIDS | 0.1-0.5 |
| C11-C15 PARETH-9 | 0.03-0.06 |
| SODIUM OLIVE AMPHOACETATE | 0.03-0.06 |
| CALCIUM PANTOTHENATE | 0.01-0.05 |
| BHA | 0.01-0.05 |
| ZEAXANTHIN | 0.001-0.01 |
| RUTIN | 0.001-0.01 |
| SPERMIDINE HCl | 0.001-0.01 |
| BIOTIN | 0.0001-0.005 |
| WATER | q.s. to 100 |

EXAMPLE 13

Styling gel with Zeaxanthin, Rutin, Spermidine, and soy isoflavones.

| Name INCI Ingredients | % w/w |
|---|---|
| Polyacrylate-14 | 0.7-2 |
| Hydroxypropyl guar | 0.5-5 |
| Sodium Hydroxymethylglycinate | 0.1-1 |
| Benzophenone-4 | 0.1-3 |
| Tetrasodium EDTA | 0.1-0.8 |
| Taurine | 0.01-0.08 |
| Calcium pantothenate | 0.01-0.05 |
| Extract of *Ajuga reptans* cell cultures with phenylpropanoid content >50% | 0.001-0.1 |
| Zeaxanthin | 0.001-0.1 |
| Rutin | 0.005-0.02 |
| Spermidine HCl | 0.001-0.05 |
| Soy isoflavones | 0.001-0.5 |
| Biotin | 0.0001-0.001 |
| Water | q.s. to 100 |

EXAMPLE 14

Fortifying airless mousse with Zeaxanthin, Rutin, Spermidine, and soy isoflavones.

| Name INCI Ingredients | % w/w |
|---|---|
| ALCOHOL | 9.5-20 |
| *BOEHMERIA NIPONONIVEA* LEAF EXTRACT | 1-5.5 |
| TAURINE | 1-5.5 |
| GLYCERIN | 1-3.5 |
| SODIUM OLIVE AMPHOACETATE | 0.5-2 |
| CALCIUM PANTOTHENATE | 0.1-2 |
| TOCOPHEROLS (α, β, γ) | 0.1-2 |
| POLYQUATERNIUM-16 | 0.02-1 |

| Name INCI Ingredients | % w/w |
| --- | --- |
| DISODIUM EDTA | 0.02-0.08 |
| *Ajuga reptans* leaf extract | 0.02-0.05 |
| SPERMIDINE HCl | 0.1-1 |
| ZEAXANTHIN | 0.1-1 |
| RUTIN | 0.1-1 |
| POTASSIUM METABISULFITE | 0.01-0.05 |
| *VITIS VINIFERA* | 0.01-0.05 |
| BIOTIN | 0.002-0.05 |
| SOY ISOFLAVONES | 0.001-0.5 |
| CITRIC ACID | 0.1-0.3 |
| WATER | q.s. to 100 |

EXAMPLE 15

Fortifying hair lotion with Zeaxanthin, Rutin, Spermidine, and soy isoflavones.

| Name INCI Ingredients | % w/w |
| --- | --- |
| Alcohol | 10.5-20 |
| *Juglans regia* extract | 1-4.5 |
| PEG-40 Hydrogenated castor oil | 0.5-3 |
| Calcium pantothenate | 0.1-0.5 |
| Perfume | 0.1-0.5 |
| Disodium EDTA | 0.05-0.1 |
| Citric acid | 0.05-0.1 |
| *Ajuga reptans* leaf extract | 0.05-0.1 |
| Spermidine HCl | 0.01-0.05 |
| Zeaxanthin | 0.1-1 |
| Rutin | 0.1-1 |
| Biotin | 0.003-0.05 |
| Lecithin | 0.002-0.005 |
| Polysorbate 80 | 0.001-0.005 |
| Soy Isoflavones | 0.001-0.5 |
| Water | q.s. to 100 |

EXAMPLE 16

Restructuring conditioner with Zeaxanthin, Rutin, Spermidine, and soy isoflavones.

| Name INCI Ingredients | % w/w |
| --- | --- |
| CETEARYL ALCOHOL | 1.5-5.5 |
| DIMETHICONE | 3-4.5 |
| GLYCERYL STEARATE | 4-5.5 |
| C12-13 ALKYL LACTATE | 1.5-3 |
| CETRIMONIUM CHLORIDE | 1-3.5 |
| PEG-100 STEARATE | 1-3.5 |
| DIMETHICONOL | 1-2.5 |
| XYLITOL | 1-2.5 |
| PHENOXYETHANOL | 0.5-1 |
| PROPYLENE GLYCOL | 0.5-1 |
| HYDROXYETHYL CELLULOSE | 0.5-1 |
| PANTHENOL | 0.5-1 |
| PERFUME | 0.5-1 |
| TRIMETHYLSILYLAMODIMETHICONE | 0.2-1 |
| PHYTANTRIOL | 0.1-1 |
| METHYLPARABEN | 0.1-1 |
| DISODIUM EDTA | 0.1-1 |
| BUTYLENE GLYCOL | 0.1-1 |
| ETHYLPARABEN | 0.01-0.05 |
| LACTIC ACID | 0.01-0.05 |
| PROPYLPARABEN | 0.01-0.05 |
| POLYGLYCERYL-3 DISTEARATE | 0.01-0.05 |
| CALCIUM PANTOTHENATE | 0.001-0.005 |
| ZEAXANTHIN | 0.0005-0.001 |
| RUTIN | 0.0005-0.001 |
| SOY ISOFLAVONES | 0.001-0.5 |
| SPERMIDINE HCl | 0.0001-0.005 |
| BIOTIN | 0.00001-0.0005 |
| WATER | q.s. to 100 |

EXAMPLE 17

Anti-hair loss mask gel with Zeaxanthin, Rutin, Spermidine, and soy isoflavones.

| Name INCI Ingredients | % w/w |
| --- | --- |
| GLYCERIN | 1.5-4.5 |
| AMMONIUM ACRYLOYL-DIMETHYL TAURATE/ VP COPOLYMER | 1-5.5 |
| CYCLOPENTASILOXANE | 1-5.5 |
| PHENOXYETHANOL | 0.1-0.8 |
| PERFUME | 0.1-0.5 |
| SILICONE QUATERNIUM-15 | 0.1-0.5 |
| TOCOPHERYL ACETATE | 0.1-0.5 |
| DIMETHICONE | 0.1-0.3 |
| METHYLPARABEN | 0.1-0.5 |
| AMMONIUM GLYCYRRHIZATE | 0.1-0.5 |
| ETHYL HEXYL METHOXYCINNAMATE | 0.05-0.1 |
| DISODIUM EDTA | 0.05-0.1 |
| ETHYLPARABEN | 0.02-0.05 |
| GLYCERYL LAURATE | 0.02-0.05 |
| CALCIUM PANTOTHENATE | 0.02-0.05 |
| PROPYLPARABEN | 0.02-0.05 |
| ZEAXANTHIN | 0.001-0.01 |
| RUTIN | 0.01-0.1 |
| SOY ISOFLAVONES | 0.001-0.5 |
| SPERMIDINE HCL | 0.0001-0.005 |
| BIOTIN | 0.0001-0.005 |
| WATER | q.s. to 100 |

EXAMPLE 18

Fortifying shampoo with Zeaxanthin, Rutin, Spermidine, and soy isoflavones.

| Name INCI Ingredients | % w/w |
| --- | --- |
| MAGNESIUM LAURETH SULFATE | 2-8.5 |
| SODIUM LAUROYL SARCOSINATE | 2-5.5 |
| DISODIUM LAURETH SULFOSUCCINATE | 1-5.5 |
| PEG-200 HYDROGENATED GLYCERYL PALMATE | 1-5.5 |
| COCAMIDE MIPA | 1-5.5 |
| GLYCERIN | 0.5-1 |
| PERFUME | 0.5-1 |
| GLYCOL DISTEARATE | 0.5-1 |
| CITRIC ACID | 0.5-1 |
| LAURETH-7 | 0.5-1 |
| PEG-7 GLYCERYL COCOATE | 0.5-1 |
| BETAINE | 0.5-1 |
| LAURYL METHYL GLUCETH-10 | 0.5-1 |
| HYDROXYPROPYLDIMONIUM CHLORIDE | |
| POLYQUATERNIUM-10 | 0.2-0.5 |
| SODIUM HYDROXYMETHYLGLYCINATE | 0.2-0.5 |
| POTASSIUM UNDECYLENOYL WHEAT PROTEIN | 0.2-0.5 |
| TETRASODIUM EDTA | 0.2-0.5 |
| PANTHENOL | 0.2-0.5 |
| SILICONE QUATERNIUM-15 | 0.1-0.5 |
| SILK AMINO ACIDS | 0.1-0.5 |
| CALCIUM PANTOTHENATE | 0.01-0.05 |
| LAURETH-4 | 0.01-0.05 |

-continued

| Name INCI Ingredients | % w/w |
|---|---|
| BHA | 0.01-0.05 |
| ZEAXANTHIN | 0.001-0.01 |
| RUTIN | 0.001-0.01 |
| SPERMIDINE HCl | 0.001-0.01 |
| SOY ISOFLAVONES | 0.001-0.5 |
| BIOTIN | 0.0001-0.005 |
| WATER | q.s. to 100 |

EXAMPLE 19

Fortifying shampoo with Zeaxanthin, Rutin, and Spermidine.

| Name INCI Ingredients | % w/w |
|---|---|
| MAGNESIUM LAURETH SULFATE | 2-8.5 |
| SODIUM LAUROYL SARCOSINATE | 2-5.5 |
| DISODIUM LAURETH SULFOSUCCINATE | 1-5.5 |
| EPIGALLOCATECHIN-3-GALLATE | 1-5.5 |
| PEG-200 HYDROGENATED GLYCERYL PALMATE | 1-5.5 |
| COCAMIDE MIPA | 0.5-1 |
| GLYCERIN | 0.5-1 |
| PERFUME | 0.5-1 |
| GLYCOL DISTEARATE | 0.5-1 |
| CITRIC ACID | 0.5-1 |
| LAURETH-7 | 0.5-1 |
| PEG-7 GLYCERYL COCOATE | 0.5-1 |
| BETAINE | 0.5-1 |
| LAURYL METHYL GLUCETH-10 HYDROXYPROPYLDIMONIUM CHLORIDE | 0.2-0.5 |
| POLYQUATERNIUM-10 | 0.2-0.5 |
| SODIUM HYDROXYMETHYLGLYCINATE | 0.2-0.5 |
| POTASSIUM UNDECYLENOYL WHEAT PROTEIN | 0.2-0.5 |
| TETRASODIUM EDTA | 0.2-0.5 |
| PANTHENOL | 0.1-0.5 |
| SILICONE QUATERNIUM-15 | 0.1-0.5 |
| SILK AMINO ACIDS | 0.01-0.05 |
| CALCIUM PANTOTHENATE | 0.01-0.05 |
| LAURETH-4 | 0.01-0.05 |
| BHA | 0.001-0.01 |
| ZEAXANTHIN | 0.001-0.01 |
| RUTIN | 0.001-0.01 |
| SPERMIDINE HCl | 0.001-0.05 |
| BIOTIN | 0.0001-0.005 |
| WATER | q.s. to 100 |

EXAMPLE 20

Fortifying hair lotion with Zeaxanthin, Rutin, and Spermidine.

| Name INCI Ingredients | % w/w |
|---|---|
| Alcohol | 10.5-20 |
| *Juglans regia* extract | 1-4.5 |
| Epigallocatechin-3-gallate | 0.5-3 |
| PEG-40 Hydrogenated castor oil | 0.1-0.5 |
| Calcium pantothenate | 0.1-0.5 |
| Perfume | 0.05-0.1 |
| Disodium EDTA | 0.05-0.1 |
| Citric acid | 0.05-0.1 |
| *Ajuga reptans* leaf extract | 0.05-0.1 |
| Spermidine HCl | 0.1-0.3 |
| Zeaxanthin | 0.1-0.5 |
| Rutin | 0.003-0.05 |
| Biotin | 0.002-0.05 |
| Lecithin | 0.001-0.05 |

-continued

| Name INCI Ingredients | % w/w |
|---|---|
| Polysorbate 80 | 0.001-0.05 |
| Soy Isoflavones | 0.001-0.5 |
| Water | q.s. to 100 |

EXAMPLE 21

Fortifying shampoo with Zeaxanthin and Spermidine.

| Name INCI Ingredients | % w/w |
|---|---|
| MAGNESIUM LAURETH SULFATE | 2-8.5 |
| SODIUM LAUROYL SARCOSINATE | 2-5.5 |
| DISODIUM LAURETH SULFOSUCCINATE | 1-5.5 |
| PEG-200 HYDROGENATED GLYCERYL PALMATE | 1-5.5 |
| COCAMIDE MIPA | 1-5.5 |
| GLYCERIN | 0.5-1 |
| PERFUME | 0.5-1 |
| GLYCOL DISTEARATE | 0.5-1 |
| CITRIC ACID | 0.5-1 |
| LAURETH-7 | 0.5-1 |
| PEG-7 GLYCERYL COCOATE | 0.5-1 |
| BETAINE | 0.5-1 |
| LAURYL METHYL GLUCETH-10 HYDROXYPROPYLDIMONIUM CHLORIDE | 0.5-1 |
| POLYQUATERNIUM-10 | 0.2-0.5 |
| SODIUM HYDROXYMETHYLGLYCINATE | 0.2-0.5 |
| POTASSIUM UNDECYLENOYL WHEAT PROTEIN | 0.2-0.5 |
| TETRASODIUM EDTA | 0.2-0.5 |
| PANTHENOL | 0.2-0.5 |
| SILICONE QUATERNIUM-15 | 0.1-0.5 |
| SILK AMINO ACIDS | 0.1-0.5 |
| CALCIUM PANTOTHENATE | 0.01-0.05 |
| LAURETH-4 | 0.01-0.05 |
| BHA | 0.01-0.05 |
| ZEAXANTHIN | 0.001-0.01 |
| SPERMIDINE HCl | 0.001-0.01 |
| LINALOOL | 0.001-0.01 |
| BIOTIN | 0.001-0.005 |
| WATER | q.s. to 100 |

EXAMPLE 22

Fortifying airless mousse with Rutin and Spermidine (without Zeaxanthin).

| Name INCI Ingredients | % w/w |
|---|---|
| ALCOHOL | 9.5-20 |
| *BOEHMERIA NIPONONIVEA* LEAF EXTRACT | 1-5.5 |
| TAURINE | 1-5.5 |
| GLYCERIN | 1-3.5 |
| SODIUM OLIVE AMPHOACETATE | 0.5-2 |
| CALCIUM PANTOTHENATE | 0.1-2 |
| TOCOPHEROLS ($\alpha,\beta,\gamma$) | 0.1-2 |
| POLYQUATERNIUM-16 | 0.02-1 |
| DISODIUM EDTA | 0.02-0.08 |
| *AJUGA REPTANS* LEAF EXTRACT | 0.02-0.05 |
| SPERMIDINE HCl | 0.01-0.5 |
| RUTIN | 0.1-1 |
| POTASSIUM METABISULFITE | 0.1-0.5 |
| VITIS VINIFERA | 0.01-0.05 |
| BIOTIN | 0.002-0.05 |
| CITRIC ACID | 0.1-0.3 |
| WATER | q.s. to 100 |

EXAMPLE 23

Fortifying hair lotion with zeaxanthin and rutin.

| Name INCI Ingredients | % w/w |
|---|---|
| Alcohol | 10.5-20 |
| *Juglans regia* extract | 1-4.5 |
| PEG-40 Hydrogenated castor oil | 0.5-3 |
| Calcium pantothenate | 0.1-0.5 |
| Perfume | 0.1-0.5 |
| Disodium EDTA | 0.05-0.1 |
| Citric acid | 0.05-0.1 |
| *Ajuga reptans* leaf extract | 0.05-0.1 |
| Zeaxanthin | 0.01-0.5 |
| Rutin | 0.1-0.3 |
| Biotin | 0.001-0.05 |
| Lecithin | 0.002-0.005 |
| Polysorbate 80 | 0.002-0.005 |
| Soy Isoflavones | 0.001-0.5 |
| Water | q.s. to 100 |

BRIEF DESCRIPTION OF THE DRAWINGS

An experimental study on the effects of the invention with reference to FIGS. 1 to 4 of the attached diagrams is now described.

These show graphics relative to the percent variation of apoptotic activity of caspase-3 in the presence of the active ingredients of the invention, as described in detail below.

The abbreviations in the graphics are defined in the following Table A.

EXPERIMENTAL STUDY

Materials and Methods
Activity of Caspase-3

The activity of caspase-3 has been assessed by using the colorimetric test ApoTarget™Caspase-3/CPP32 with DEVD-pNA as the substrate (BioSource International, Camarillo, Calif.). DEVD-pNA consists of a chromophore group (p-nitroanilide (p-NA) and a synthetic tetrapeptide (DEVD-Asp-Glu-Val-Asp) that represents the consensus sequence for the proteolytic cut catalyzed by caspase-3. The test was carried out by following the specifications indicated by the manufacturer in detail, using an equal amount of total protein (200 µg) for every sample.

Every sample was tested in duplicate. The activity was assessed by measuring the absorbance at 405 nm (in the graphics, ABS 405 nm) with an automatic spectrometer for 96-well plates (MPT Reader DV990 BVG) that carries out a double reading for every well.

Cell Lysis

Cellular lysis is a technique applied to extract all of the proteins in the cultured cells to be analyzed. Various lysis protocols exist: the one used in the experimental tests described here consists of the use of a highly denaturing buffer (lysis buffer, provided within the kit for the test of the caspase-3 activity). After incubation with the various active ingredients, the lysis buffer is placed onto the cell plates, a scraper is then used directly on the layer of cells to help collect the largest quantity possible. The protein extraction is then improved with incubation on ice (4° C.) for 10 minutes. The cellular debris are precipitated with centrifugation at 10,000×g for 1 minute. The lysates are retrieved and frozen at −80° C.

Protein Assay: Lowry-Ciocalteau Method

A spectrometer is used to determine the concentration of proteins by measuring the absorbance of monochromatic light from a substance. This value is a function of the number of molecules encountered by the light beam, which in turn depends on two factors: the thickness of the solution that the light passes through (usually a cuvette with a thickness of one centimeter is used) and the concentration of the substance under examination. To carry out the determination, a calibration line is constructed in which the variation of the absorbance as a function of a known quantity of a protein under standard assay conditions is reported. The points should, without experimental error, lie on a line passing through the origin. By putting the absorption value of an unknown sample on the y-axis of this standard curve, it is possible to read the corresponding concentration of the sample under examination on the x-axis. Duplicates are used for both the samples and the standard line. A standard line is constructed using BSA.

The spectrophotometric reading of the absorbance is carried out at a wavelength of 605 nm of the product of the reaction between the Folin-Ciocalteau reagent, a solution of sodium salts of tungstic, molybdic, and phosphoric acid, and the alcohol groups of the protein tyrosines in the presence of $Cu^{2+}$ ions. The chemical basis for the formation of color is the reduction of the Folin-Ciocalteau reagent produced by the copper ions.

Assessment of the Anti-apoptotic Activity of Zeaxanthin, Rutin, and Spermidine: Inhibition of the Activation of the Caspase-3 Enzyme.

The anti-apoptotic effects of the invention's active ingredients, Zeaxanthin, Rutin, and Spermidine, were studied in HFDPC-c cells (PromoCell®) maintained in culture in the presence of Follicle Dermal Papilla Growth Medium, and following the manufacturer's indications (PromoCell®).

The activity of caspase-3 was assessed by using the colorimetric assay ApoTarget™Caspase-3/CPP32, and the concentration of the protein was assessed by using the Lowry-Ciocalteau method and a BSA standard as described above.

Results

In HFDPC-c cells the induction of apoptosis, evidenced by the increase in caspase-3 activity, was obtained through a 24-hour incubation of the cells with Staurosporine (1 µM), as shown in FIG. 1.

The activity of the invention's various active ingredients was assessed by adding them, at different concentrations as specified in the following Table A, to the cell culture medium immediately after the addition of Staurosporine (1 µM). The incubation was also maintained for 24 hours in this case.

At the end of the incubation the plates in which the cells were cultivated were laid out on a bed of ice, washed once in cold PBS and incubated in the lysis buffer. After the lysis, the protein assay and the caspase-3 activity test was carried out.

TABLE A

Active ingredients used in the caspase-3 activity assessment tests

| Active ingredient | [µM] | [µg/ml] |
|---|---|---|
| Spermidine* (S) | 0.1 | 0.026 |
|  | 1 | 0.264 |
| Rutin (R) | 2 | 1.34 |
|  | 20 | 13.42 |
| Zeaxanthin (Z) | 0.4 | 4.54 |
|  | 4 | 45.44 |
|  | 2 | 22.72 |
|  | 1 | 11.36 |

*Used as spermidine trihydrochloride

The effect on caspase-3 activity was assessed after incubations with the active ingredients used individually, one at a time as shown in FIG. 2 and in various combinations amongst themselves as shown in FIG. 3 (pairs) and FIG. 4 (triads).

In Table B the data of the percentage change in caspase-3 activity obtained for the individual active ingredients and their combinations is reported, related to 100% activity for 1 μM Staurosporine.

In the active ingredient column, for example, R 2 indicates Rutin at a concentration of 2.2 μM; R 20 indicates Rutin at a concentration of 22 μM, and so on as specified above in Table A. For example, R 2+S 1+Z 4 indicates a ternary combination in which Rutin is present at a concentration of 2.2 μM; Spermidine is present at a concentration of 1 μM; Zeaxanthin is present at a concentration of 80 μM. The combination R 2+S 1+Z 4 corresponds to Rutin=2.5 mg pure active ingredient; Spermidine=0.5 mg pure active ingredient; Zeaxanthin=4 mg pure active ingredient, with a relative weight relationship R:S:Z=5:1:8. Similarly, S 1+R 2+Z 2 corresponds to Rutin=2.5 mg pure active ingredient; Spermidine=0.5 mg pure active ingredient; Zeaxanthin=2 mg pure active ingredient, with a relative weight relationship R:S:Z=5:1:4.

inhibition value of the caspase activity is noted for the pair Zeaxanthin+Rutin (see R 20+Z 4 providing 59.05% inhibition).

In the case of ternary combinations, the activity of the triad R+S+Z is particularly notable inasmuch as Zeaxanthin added to the R+S pair improves the % inhibition of the caspase activity in a comparable way even at a low concentration, see for instance the case of Z 0.4 (50.4% inhibition) and Z 4 (59.79% inhibition) in a ternary association with the pair R 20+S 0.1.

Synergy is therefore observed among the active ingredients even independently of their increased concentration.

Clinical Study for the Cure of Androgenetic Alopecia and Telegen Effluvium

Rationale

From the above assessments, a composition of the invention has been subjected to clinical study to evaluate its capacity to control the cellular senescence and apoptosis processes in the hair follicles that trigger hair loss in humans.

In trichological diseases such as androgenetic alopecia, telogen effluvium, and alopecia areata, the various cellular components that compose the hair follicle undergo an apoptotic process induced by the alteration of cellular control mechanisms including the systems for the exchange of cellular messages (gap junctions) and the initiation of the caspase cascade within DNA.

This premature aging of the dermal papilla of the follicle provoked by oxidative stress is combined with various specific factors, and in particular with the interaction of the follicular androgen receptors in male and female androgenetic alopecia.

TABLE B

Percent inhibition of caspase-3 activity

| | Staurosporine | Active ingredients [μM] | Corresponding to mg | % Caspase-3 activity | % Inhibition of caspase activity |
|---|---|---|---|---|---|
| 1 | ST 1 μM | // | // | 100 | 0 |
| 2 | ST 1 μM | S0.1 | 0.05 | 78.36 | 21.64 |
| 3 | ST 1 μM | S1 | 0.5 | 63.10 | 36.90 |
| 4 | ST 1 μM | R2 | 2.5 | 67.90 | 32.10 |
| 5 | ST 1 μM | R20 | 25 | 53.73 | 46.27 |
| 6 | ST 1 μM | Z0.4 | 0.4 | 71.00 | 29.00 |
| 7 | ST 1 μM | Z4 | 4 | 86.80 | 13.20 |
| 8 | ST 1 μM | R2 + Z0.4 | 2.5 + 0.4 | 71.67 | 28.33 |
| 9 | ST 1 μM | R2 + S0.1 | 2.5 + 0.05 | 57.68 | 42.32 |
| 10 | ST 1 μM | R20 + Z0.4 | 25 + 0.4 | 65.87 | 34.13 |
| 11 | ST 1 μM | R20 + Z4 | 25 + 4 | 40.95 | 59.05 |
| 12 | ST 1 μM | S0.1 + Z0.4 | 0.05 + 0.4 | 64.84 | 35.16 |
| 13 | ST 1 μM | S0.1 + Z4 | 0.05 + 4 | 54.61 | 45.39 |
| 14 | ST 1 μM | S1 + R20 | 0.5 + 25 | 75.09 | 24.91 |
| 15 | ST 1 μM | S1 + Z0.4 | 0.5 + 0.4 | 71.67 | 28.33 |
| 16 | ST 1 μM | S1 + Z4 | 0.5 + 4 | 62.11 | 37.89 |
| 17 | ST 1 μM | R2 + Z4 | 2.5 + 4 | 54.89 | 45.11 |
| 18 | ST 1 μM | R20 + S0.1 | 25 + 0.05 | 60.14 | 39.86 |
| 19 | ST 1 μM | R2 + S0.1 + Z0.4 | 2.5 + 0.05 + 0.4 | 48.25 | 51.75 |
| 20 | ST 1 μM | R 2 + S 0.1 + Z 4 | 2.5 + 0.05 + 4 | 51.70 | 48.30 |
| 21 | ST 1 μM | R20 + S0.1 + Z0.4 | 25 + 0.05 + 0.4 | 49.60 | 50.40 |
| 22 | ST 1 μM | R20 + S0.1 + Z4 | 25 + 0.05 + 4 | 40.21 | 59.79 |
| 23 | ST 1 μM | R2 + S1 + Z0.4 | 2.5 + 0.5 + 0.4 | 44.70 | 55.30 |
| 24 | ST 1 μM | R2 + S1 + Z4 | 2.5 + 0.5 + 4 | 46.80 | 53.20 |
| 25 | ST 1 μM | R20 + S1 + Z0.4 | 25 + 0.5 + 0.4 | 68.53 | 31.47 |
| 26 | ST 1 μM | R20 + S1 + Z4 | 25 + 0.5 + 4 | 61.53 | 38.47 |
| 27 | ST 1 μM | R2 + S1 + Z2 | 2.5 + 0.5 + 2 | 48.40 | 51.60 |
| 28 | ST 1 μM | R2 + S1 + Z1 | 2.5 + 0.5 + 1 | 47.30 | 52.70 |

Legend:
ST = Staurosporine
Z = Zeaxanthin
R = Rutin
S = Spermidine trihydrochloride Discussion By referring to above Table B and the diagrams for a detailed assessment of the activity, it can be seen that:

Some pairs of active ingredients (such as for instance, the S 0.1+Z 4 pair) were more effective and superior in their anti-apoptotic activity with respect to the individual active ingredients at the same concentration, demonstrating synergy. Among the tested pairs, the highest %

Materials and Methods

An open clinical trial was conducted and carried out on 50 subjects (26 women, 24 men) suffering from telogen effluvium and male and female androgenetic alopecia. Healthy volunteers between 20 and 45 years old suffering from androgenetic alopecia and telogen effluvium were recruited according to the standardized inclusion and exclusion criteria for this type of trial (absence of internal and endocrine diseases, pregnancy, assumption of endocrinological drugs or subjection to endocrinological therapies, simultaneous systemic or topical trichological therapy for less than six months).

The study was carried out in an open way through the administration of tablets of a composition according to the invention containing R2+S1+Z2, which corresponds to Rutin=2.5 mg pure active ingredient; Spermidine trihydrochloride=0.5 mg pure active ingredient; Zeaxanthin=2 mg pure active ingredient, with a weight ratio of R:S:Z=5:1:4.

Every subject received a dosage necessary for 3 months of treatment.

The characteristics of the subjects at the time of the baseline recruitment are reported in Table C.

TABLE C

| | |
|---|---|
| No. of subjects | 50 |
| Age (average years) | 34 ± 0.3 |
| Age at which the subject began losing hair (average years) | 22 ± 0.5 |
| % of subjects with family history of Androgenetic Alopecia | 28 |

Clinical Evaluation

The dermatological clinical evaluation of the subjects was carried out to determine the diagnosis and the degree of androgenetic and telogen effluvium baldness, and an improvement or worsening score was defined starting from the time of recruitment, or the baseline, until an intermediate time and the final control, according to:

$T_0$=baseline;
$T_1$=intermediate control
$T_2$=final control

The evaluation was carried out according to the standardized score used in most clinical trials of this type:
Strong worsening (−3)
Strong improvement (+3)
Good worsening (−2)
Good improvement (+2)
Light worsening (−1)
Light improvement (+1)
No change (0)

The parameters used for the clinical evaluation were: the evaluation of the percent of anagen through dermatoscopy, the diameter of the hair shaft, and a pull test for the evaluation of the extent of detachment of the hair from the scalp. The percent of follicles in the anagen phase was evaluated through the dermatoscopy technique, considered the most reliable and least invasive. The diameter of the hair shaft was measured at $T_0$, $T_1$ and $T_2$. The shaft diameter indicates the clinical state of the progression of androgenetic baldness, where miniaturization is one of the pathognomonic symptoms. The diameter of the shaft is also an index for the follicle's state of distress for establishing an apoptotic process in the dermal papilla and the epithelial components of the matrix.

Increase in the anagen phase: in the presence of trichological pathology, the anagen phase in the hair follicles tends to be shorter due to the modification of the Hair Cycle Clock control mechanisms. The decrease of anagen determines the fast passage of the follicle to progressive cell death phases (catagen, telogen) induced by cellular apoptotic processes (mainly via induction of the caspase cascade).

For this reason, the increase in the anagen phase during trichological therapy is an evident indicator of the positive effect of the substances used on the life of hair follicle cells.

Finally, the pull test evaluation indicates the severity of hair loss, considering the number of hairs collected after a determined traction by the operator: the hairs that have lost adhesion with the dermal and epidermal layers are removed. The greater the amount of hair removed per every pull, the greater the severity of the hair loss. A decrease in hairs pulled per test indicates a reduction in hair loss.

Finally, an assessment of any cutaneous or systemic side effects was carried out through a dermatological exam and any other investigations deemed necessary.

Results

The summary of the average data obtained at the baseline ($T_0$) is reported in the following Table D.

TABLE D

| | |
|---|---|
| Hair shaft diameter (average mm) | 0.5 |
| Anagen (average) | 65% |
| Clinical evaluation (% improvement) | = |
| Pull test (average score) | 3 |

The summary of the average data obtained at the intermediate time ($T_1$) is reported in the following Table E.

TABLE E

| | |
|---|---|
| Hair shaft diameter (average mm) | 0.7 |
| Anagen (average) | 72% |
| Clinical evaluation (% improvement) | 70% |
| Increase in hair shaft diameter: no. of subjects) | 35 (70%) |
| Pull test (average score) | 1 |

The summary of the average data obtained at the final time ($T_2$) is reported in the following Table F.

TABLE F

| | |
|---|---|
| Hair shaft diameter (average mm) | 0.8 |
| Anagen (average) | 84% |
| Clinical evaluation (% improvement) | 88% |
| Increase in hair shaft diameter: (no. of subjects) | 43 (86%) |
| Pull test (average score) | 0 |

The data demonstrate the improvement in all of the parameters evaluated in the patients subjected to treatment with the invention's composition.

In particular:

The increase of the shaft diameter is statistically significant, passing from an average value of 0.5 mm (mean) at $T_0$ to 0.8 mm (mean) at $T_2$, an index of the stimulus of the elongation of the dermal papilla's anagen phase (62% increase in the shaft diameter). This result was obtained in 86% of the subjects treated with the invention. It is also interesting to note that the positive response was sufficiently fast: 70% of the clinical improvement evaluation and 35 subjects out of 50 (70%) already at $T_1$.

In this regard, the average value of anagen in the subjects treated at $T_0$ was 65%, passing to 72% at $T_1$ (+6.9%), and 84% at $T_2$ (+22.6%).

The final judgment of the dermatological clinical evaluation reflects the results of the data obtained. The overall improvement with respect to the scores defined as strong improvement and good improvement is assessed at a rate of 86% of the subjects. If a modest improvement is also considered as a positive result, the percent of subjects who have benefited from treatment with the invention reaches 92%. The clinical improvement evaluation score is reported in Table G.

TABLE G

|  | No. Subjects |
|---|---|
| Strong improvement | 27 |
| Good improvement | 16 |
| Light improvement | 3 |
| No variation | 1 |
| Light worsening | 2 |
| Severe worsening | 1 |

PULL TEST: the data have shown a sharp decrease in hair loss in 43 of the 50 subjects tested (86%). The average values of the test are reported in the following Table H:

TABLE H

|  | Pull test | | |
|---|---|---|---|
|  | $T_0$ | $T_1$ | $T_2$ |
| Score | 3 | 1 | 0 |

0 = no loss
1 = minimum loss
2 = copious loss
3 = severe loss

Discussion

The data obtained from the clinical trial reported above demonstrate a remarkable improvement in the parameters considered significant for assessing the severity of a trichological disease, namely:

the increase in the diameter of the hair shaft
the modification of the anagen phase
dermatological clinical improvement
improvement of the pull test The increase in the diameter of the hair shaft was decidedly significant in 86% of the subjects treated, evidence of an improvement in the follicles' state and the elongation of the anagen phase, also considering the net increase in the percent of follicles in anagen at the end of treatment.

The improvement in the pull test was equally obvious, with a reduction from an average value of score 3 at $T_0$ to an average value of 0 at $T_2$ in 86% of the subjects evaluated in the study.

Finally, no systemic side effects were detected in the treated patients.

The invention's composition therefore represents a valid therapeutic means in androgenetic alopecia and telogen effluvium.

To complement the clinical results obtained and described above, the following Table L is reported for the comparison of the data discussed above for the invention (R2+S1+Z2) with corresponding data obtained in an analogous clinical study with the administration of a composition according to the prior art (EP 1469843 of the same Applicants) containing only 0.5 mg/tablet spermidine as an active ingredient, identified in Table L as S1.

TABLE L

|  | $T_0$ | $T_1$ | $T_2$ |
|---|---|---|---|
|  | % hair bulbs in anagen phase | | |
| S1 | 59% | 64% | 71% |
| R2 + S1 + Z2 | 65% | 72% | 84% |
|  | Pull test score | | |
| S1 | 1.8 | 0.1 | 0.2 |
| R2 + S1 + Z2 | 3 | 1 | 0 |
|  | anagen variation | | |
| S1 | = | +8% | +20% |
| R2 + S1 + Z2 | = | +11% | +29% |
|  | pull test variation | | |
| S1 | = | −94% | −89% |
| R2 + S1 + Z2 | = | −67% | −100% |

$T_0$ = basal
$T_1$ = intermediate control
$T_2$ = final control

This comparison shows a significant improvement of all of the underlying parameters described above by the invention.

The invention claimed is:

1. A method for treating scalp disorders in a human comprising:
   administering a composition topically or orally to the human, wherein the composition comprises an active ingredient selected from the group consisting of zeaxanthin with rutin, zeaxanthin with spermidine, and zeaxanthin with rutin and spermidine.

2. The method of claim 1 wherein the scalp disorders consist of chemotherapy-induced alopecia, alopecia areata, androgenic alopecia and telogen effluvium.

3. A pharmaceutical, dietary, or cosmetic composition to treat of scalp disorders selected from the group consisting of chemotherapy-induced alopecia, alopecia areata, androgenic alopecia and telogen effluvium, wherein the composition consists essentially of an active ingredient selected from the group consisting of zeaxanthin with rutin, zeaxanithin with spermidine, and zeaxanthin with rutin and spermidine, being effective on treatment of scalp disorders through a combined action of caspase-3 inhibitaion and related anti-apoptotic activity and thereby resulting in an increase in the diameter of hair shaft, enlongation of the anagen phase and an improved score in hair pull test, and an excipient for topical administration on the scalp or for oral administration.

4. The composition according to claim 3, wherein the active ingredient is zeaxanthin and rutin.

5. The composition according to claim 4, wherein the active ingredient is zeaxanthin in a quantity of 0.2 mg to 10 mg and rutin in a quantity of 0.5 mg to 25 mg.

6. The composition according to claims 3, wherein the active ingredient is zeaxanthin, rutin and spermidine.

7. The composition according to claim 6, wherein the active ingredient is zeaxanthin in quantities of 0.2 mg to 10 mg, rutin in quantities of 0.5 mg to 25 mg and spermidine in quantities of 0.05 to 0.5 mg.

8. The composition according to claim 7, wherein the active ingredient is zeaxanthin, rutin, and spermidine in a 4:5:1 ratio by weight, respectively.

9. The composition according to claim 3, wherein the active ingredient is zeaxanthin and spermidine.

10. The composition according to claim 9, wherein the active ingredient is zeaxanthin in quantities of 0.2 mg to 10 mg and spermidine in quantities of 0.05 to 0.5 mg.

11. The composition according to claim 3 characterized by comprising excipients for topical administration on the scalp.

12. The composition according to claim 11, wherein the active ingredient is 0.0005-1% w/w Zeaxanthin.

13. The composition according to claim 11, wherein the active ingredient is 0.0005-1% w/w Zeaxanthin and 0.0001-1% w/w Spermidine trihydrochloride.

14. The composition according to claim 11, wherein the active ingredient is 0.0005-1% w/w Zeaxanthin, 0.0005-1% w/w Rutin, and 0.0001-1% w/w Spermidine trihydrochloride.

15. A composition according to claim 3 characterized by comprising excipients for oral administration.

16. The composition according to claim 15, wherein the active ingredient is, per unit of oral administration, 2 mg zeaxanthin, 2.5 mg rutin, and 0.285 mg spermidine (corresponding to 0.5 mg of spermidine trihydrochloride).

17. The composition according to claim 15, wherein the active ingredient is per unit of oral administration, 0.2-10 mg zeaxanthin.

18. The composition according to claim 15, wherein the active ingredient is, per unit of oral administration, 2.50-12 mg rutin.

* * * * *